United States Patent [19]
Heyse et al.

[11] Patent Number: 5,406,014
[45] Date of Patent: Apr. 11, 1995

[54] DEHYDROGENATION PROCESSES, EQUIPMENT AND CATALYST LOADS THEREFOR

[75] Inventors: John V. Heyse, Crockett; Paul G. Johnson, Pinole; Bernard F. Mulaskey, Fairfax, all of Calif.

[73] Assignee: Chevron Research and Technology Company, San Francisco, Calif.

[21] Appl. No.: 177,124

[22] Filed: Jan. 4, 1994

Related U.S. Application Data

[63] Continuation-in-part of Ser. No. 283, Jan. 4, 1993, abandoned.

[51] Int. Cl.$^6$ .................................... C07C 5/333
[52] U.S. Cl. .................... 585/444; 585/443; 585/654
[58] Field of Search ............. 585/443, 444, 654

[56] References Cited

U.S. PATENT DOCUMENTS

| | | |
|---|---|---|
| 3,531,394 | 9/1970 | Kuszman . |
| 3,531,543 | 9/1970 | Clippinger et al. . |
| 3,584,060 | 6/1971 | Rausch . |
| 3,631,215 | 12/1971 | Clippinger et al. . |
| 3,864,284 | 2/1975 | Clippinger et al. . |
| 3,878,131 | 4/1975 | Hayes . |
| 4,167,532 | 9/1979 | Walker et al. . |
| 4,191,846 | 3/1980 | Farha, Jr. et al. . |
| 4,208,302 | 6/1980 | McKay . |
| 4,264,433 | 4/1981 | McKay . |
| 4,268,188 | 5/1981 | Bertus . |
| 4,404,087 | 9/1983 | Reed . |
| 4,438,288 | 3/1984 | Imai . |
| 4,447,316 | 5/1984 | Buss . |
| 4,456,527 | 6/1984 | Buss et al. . |
| 4,507,196 | 3/1985 | Reed . |

(List continued on next page.)

FOREIGN PATENT DOCUMENTS

| | | |
|---|---|---|
| 0192059 | 8/1986 | European Pat. Off. . |
| 0351067 | 1/1990 | European Pat. Off. . |
| 2162082A | 1/1986 | United Kingdom . |
| 2234530A | 2/1991 | United Kingdom . |

OTHER PUBLICATIONS

Shinohara, Kohchi, Shibata, Sugitani and Tsuchida; "Development of nondestructive technique for measuring carburization thickness and a new carburization-resistant alloy"; Werkstoffe und Korrosion, 1986; pp. 410–411.

Alon Processing, Inc.; "Alonized Steels for high temperature corrosion resistance"; 1990; pp. 1–19.

Micron, Inc., Analytical Service Laboratory; "Report #R-8126, Alonized Steel"; Jun. 1985.

W. A. McGill and M. J. Weinbaum, "The Selection, Application and Fabrication of Alonized Systems in the Refinery Environment"; 1975; pp. 1–18.

Pujado et al., "Make $C_3$–$C_4$ Olefins Selectively"; Hydrocarbon Processing; pp. 65–70; Mar. 1990.

Dunn, "HP In Construction"; Hydrocarbon Processing; pp. 41–42; Aug. 1991.

Pujado et al., "Production of LPG Olefins by Catalytic (List continued on next page.)

*Primary Examiner*—Asok Pal
*Attorney, Agent, or Firm*—Burns, Doane, Swecker & Mathis

[57] ABSTRACT

Disclosed are methods for dehydrogenation of alkanes into alkenes in reactor systems of improved resistance to carburization under dehydrogenation conditions. The reactor walls are provided with a carburization and abrasion resistant protective layer by applying a metal plating, cladding or other coatings, such as painting, of a metal, such as Sb, As, Bi, Cu, Cr, Ga, Ge, In, Pb, Se, Te, Sn, particularly tin as a stannide layer, for forming a carburation resistant protective layer to a thickness of about 0.5 to 15 mils, effective to isolate the steel portion from hydrocarbons during the dehydrogenation process while avoiding any substantial liquid metal embrittlement. The protective layer is formed anchored to the steel portion through an intermediate carbide-rich bonding layer.

52 Claims, 1 Drawing Sheet

U.S. PATENT DOCUMENTS

| | | |
|---|---|---|
| 4,511,405 | 4/1985 | Reed . |
| 4,545,893 | 10/1985 | Porter . |
| 4,551,227 | 10/1985 | Porter . |
| 4,552,643 | 11/1985 | Porter . |
| 4,595,673 | 6/1986 | Imai et al. . |
| 4,613,372 | 9/1986 | Porter . |
| 4,665,267 | 5/1987 | Barri . |
| 4,666,583 | 5/1987 | Porter . |
| 4,686,201 | 8/1987 | Porter . |
| 4,687,567 | 8/1987 | Porter . |
| 4,692,234 | 9/1987 | Porter et al. . |
| 4,716,143 | 12/1987 | Imai . |
| 4,727,216 | 2/1988 | Miller . |
| 4,786,625 | 11/1988 | Imai et al. . |
| 4,795,732 | 7/1989 | Barri . |
| 4,804,487 | 2/1989 | Reed . |
| 4,827,072 | 5/1989 | Imai et al. . |
| 4,863,892 | 9/1989 | Porter . |
| 4,902,849 | 2/1990 | McKay et al. . |
| 4,917,969 | 4/1990 | Pircher . |
| 4,926,005 | 5/1990 | Olbrich et al. . |
| 4,982,047 | 1/1991 | Barri et al. . |
| 5,012,027 | 4/1991 | Abrevaya et al. ............ 585/443 |
| 5,015,358 | 5/1991 | Reed . |

OTHER PUBLICATIONS

Dehydrogenation"; Energy Progress; vol. 4, No. 3; pp. 186–191; Sep. 1984.

Pujado et al., "OGJ Report"; Oil and Gas Journal; pp. 71–74; Mar. 1983.

Berg et al., "Catalytic LPG Dehydrogenation Fits in '80's Outlook"; Oil and Gas Journal; pp. 191–197; Nov. 1980.

Gussow et al., "Dehydrogenation Links LPG to More Octanges"; Oil and Gas Journal; pp. 96–101; Dec. 1980.

Tokyo Engineering Corp. and Kubota; "CORET, New Cracking Tube to Retard Coke Depositions"; Mar. 1986; pp. 1–5.

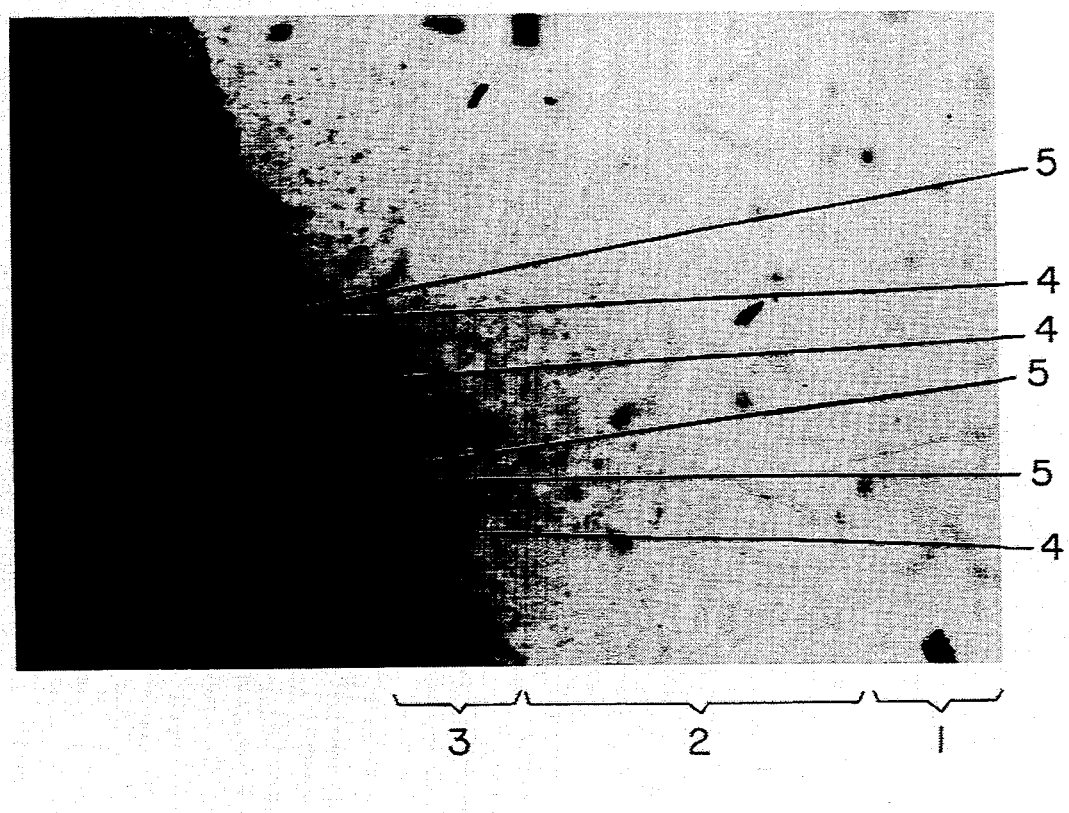

DEHYDROGENATION PROCESSES, EQUIPMENT AND CATALYST LOADS THEREFOR

CROSS-REFERENCE TO RELATED APPLICATIONS

This application is a continuation-in-part of U.S. patent application Ser. No. 08/000,283 filed Jan. 4, 1993, now abandoned, the contents of which are hereby incorporated by reference.

BACKGROUND OF THE INVENTION

The invention relates to an improved technique for the dehydrogenation of hydrocarbons, particularly light hydrocarbons. In preferred embodiments, the invention provides improved techniques for producing isobutylenes through the dehydrogenation of butanes, and propylene through the dehydrogenation of propane; particularly such techniques which minimize metal carburization and associated coke formation during dehydrogenation.

Dehydrogenation processes are of particular interest to the petroleum industry because light hydrocarbons such as butane are low-value by-products from refining operations. Butane can be converted to butylenes through dehydrogenation, which can then be used to produce MTBE.

Conventionally, butylenes, including isobutylene, have been obtained as a by-product from refinery processes such as catalytic or thermal cracking units. However, the demand for isobutylene has so far exceeded the production from such refining operations. Therefore, various alternative processes have been developed to provide isobutylene.

One type of process is the non-catalytic thermal dehydrogenation of organic compounds, e.g., the conversion of butane to butene. However, the effective use of such methods is limited due to the extensive and undesirable side reactions which occur.

Various catalytic processes have been developed in order to minimize side reaction activity and improve conversion and selectivity to desired products. Traditional catalytic dehydrogenation processes include the Air Products Catofin ™ process, the Universal Oil Products (UOP) Oleflex ™ process and the Phillips Star ™ process.

The Air Products Catofin ™ process allows for the dehydrogenation of butane to form butylene in the presence of a catalyst containing a chromic oxide supported on alumina in an adiabatic reactor. See, e.g., European Patent Application 192,059 and UK Patent Application GB 2,162,082, the contents of which are hereby incorporated by reference.

The UOP Oleflex ™ process allows for the dehydrogenation of propane to form propylene and of (iso)-butane to form (iso)butylene in the presence of a catalyst containing platinum supported on alumina in a moving bed reactor. The moving bed reactor allows continuous catalyst regeneration under the more severe conditions of lower alkane dehydrogenation. The catalyst flows fully from the reactors to the regeneration zone and is then recycled to the reactor. See, e.g., U.S. Pat. Nos. 3,584,060; 3,878,131; 4,438,288; 4,595,673; 4,716,143; 4,786,265; and 4,827,072, the contents of which are hereby incorporated by reference.

The Phillips Star ™ process allows for the dehydrogenation of butane to form butylene in the presence of a promoted platinum catalyst supported on a zinc-alumina spinel. The catalyst is supported in tubular catalyst beds located within furnaces to provide the endothermic heat of reaction. This arrangement allows for operation under isothermal conditions. Catalysts are regenerated by oxidation in air. See, e.g., U.S. Pat. Nos. 4,167,532; 4,902,849; and 4,926,005, the contents of which are hereby incorporated by reference.

Since dehydrogenation of hydrocarbons is an endothermic reaction and conversion levels are limited by chemical equilibrium, it is desirable to operate at high temperatures and low pressures. High temperatures and low pressures shift the equilibria favorably toward dehydrogenated products. However, conventional dehydrogenation catalysts suffer rapid deactivation by coking under these severe conditions. In particular, it has been found that slow accumulation of carbon deposits reduces the dehydrogenation activity of conventional dehydrogenation catalysts. Thus, conventional carbon burn-off cycles are typically used to regenerate the catalyst system after sufficient accumulation of carbon on the catalyst. In addition, sulfur compounds and hydrogen are usually introduced to the reactor feed in order to prevent carbon build-up in the reactor and catalyst bed.

Industry reports suggest that design inadequacies still exist with commercial scale dehydrogenation processes. For example, as recently reported in Platt's International Petrochemical Report (October 1993), those familiar with the UOP Oleflex ™ process say that there is a design flaw which causes a coking problem with the heat exchangers after about a year of operation.

SUMMARY OF THE INVENTION

While carbon burn-off cycles and sulfur and hydrogen addition are effective means for removing and reducing carbon deposits, they have inherent problems. First, reactors must be shut down to burn off carbon deposits. Further, the addition of hydrogen and especially sulfur requires additional process equipment, operation and cost, not to mention the hazards involved with their use. Furthermore, temporary sulfur and/or hydrogen outages are frequent due to equipment failure. The inventors believe, that not only is coking a problem, but carburization and metal-dusting are also problems.

With conventional dehydrogenation techniques using feeds containing sulfur, e.g., 50–100 ppm sulfur, carburization is not a significant problem. Apparently, the added sulfur present in these systems effectively inhibits carburization. Somehow, the sulfur interferes with the carburization reaction. But with low sulfur systems or with sulfur outages, this inherent protection no longer exists.

The problems associated with carburization normally begin with embrittlement of the physical system. The embrittlement of the steel walls leads to "metal-dusting", i.e., a release of catalytically active particles and metal droplets of metal due to an erosion of the metal. The excessive "metal-dusting" adds active metal particulates to the system, which particulates provide sites for catalytic coke formation in the system. Larger coke deposits, so-called "cokeballs" develop and can plug reactors.

This significant source of coke formation excessively aggravates the problem of coking. In fact, active metal particulates in coke particles metastasize coke generally throughout the system. That is, the active metal particulates actually induce coke formation on themselves and anywhere that the particles accumulate in the system resulting in coke-plugging of the reactor system which can lead to a premature shut-down of the system. Conventional techniques for addressing coke formation are not effective as they do not address the carburization and metal dusting phenomena.

Consequently, there is a need in the art for an improved process for the production of olefins via catalytic dehydrogenation such as starting materials needed to make MTBE, and in particular, for the dehydrogenation of dehydrogenatable hydrocarbons with reduced carburization, especially when dehydrogenation is conducted in the absence of added sulfur and/or hydrogen. Such a method would include means for inhibiting the undesirable metal embrittlement which causes carburization and ultimately the premature plugging of reactor systems and fouling of catalysts which results due to metal dusting and carburization.

Accordingly, one object of the invention is to provide improved methods for dehydrogenating a dehydrogenatable hydrocarbon. Such a method includes providing metallic protective layers which impart long-term carburization, embrittlement, coking and metal-dusting protection to metal surfaces even at the higher skin temperatures of furnace tubes used in dehydrogenation systems (typically up to 1200° F. to 1450° F., as compared to other conversion systems such as reforming which exhibit lower skin temperatures of typically between 1000° F. and 1150° F.). This protection includes prevention of the catalytic coke formation associated with carburization and metal-dusting; the prevention of which is believed to be important for on-stream life, and for addressing those industry acknowledged problems associated with commercial scale processes.

The inventors have discovered that simply providing a protective plating, cladding or other coating such as a paint to a reactor system would not be sufficient to effectively address the problem. Such a protective layer must be of sufficient thickness to provide a complete, uninterrupted coating of the underlying base metal, and it must remain complete over time. Even minor imperfections, pinholes or other flaws in the protective layer can provide destructive carburization sites sufficient to shut-down operation.

An effective protective layer must resist deleterious chemical alteration, as well as peeling and/or splitting. Additionally, it has been found that the protective layer must be applied to a thickness sufficient to completely cover the surface to be protected, and must maintain its integrity through operation. As such, the protective coating must be sufficiently abrasion resistant during catalyst loading and start-up. And since moving bed catalyst systems are common to some new dehydrogenation processes, the protective layer is preferably resistant to the abrasive effects of the catalyst moving through the reactor, as well.

Among other factors, the above and other objects of the invention can be obtained through the use of an intermediate bonding layer which anchors the protective layer to the steel substrate to be protected.

The invention, therefore, is directed to a method for dehydrogenating hydrocarbons in a reactor system comprising a steel portion, preferably a stainless steel portion, having provided thereon a protective layer to isolate the steel portion from hydrocarbons, preferably a stannide layer, applied to a thickness effective for completely isolating the steel portion from the hydrocarbon environment, while avoiding any substantial liquid metal embrittlement. The protective layer is anchored to the steel substrate through an intermediate carbide-rich (relative to the underlying steel), bonding layer; in the case of stainless steel, an intermediate carbide-rich, nickel-depleted (relative to the underlying steel), bonding layer.

In the case of a stannide outer protective layer and a stainless steel substrate, the stannide layer is nickel-enriched and comprises carbide inclusions, while the intermediate carbide-rich, nickel-depleted bonding layer comprises stannide inclusions. Preferably the carbide inclusions are continuous extensions or projections of the carbide-rich, nickel-depleted bonding layer as they extend, substantially without interruption, from the intermediate carbide-rich, nickel-depleted bonding layer into the stannide layer, and the stannide inclusions are likewise continuous extending from the stannide layer into the intermediate carbide-rich, nickel-depleted bonding layer. The aforementioned presence of carbide inclusions in the stannide layer, and stannide inclusions in the intermediate carbide-rich, nickeldepleted bonding layer, provide improved anchoring of the protective layer thereby increasing abrasion resistance. The interface between the intermediate carbide-rich, bonding layer and the nickel-enriched stannide layer is irregular, but is otherwise substantially without interruption.

Although there is a need to ensure a complete coating of the underlying base metal to be protected, applying excessive amounts or thicknesses of the material used to form the protective layer must also be avoided. If the layer is too thick, for example, where the alloying materials of a paint have locally pooled prior to curing, liquid metal embrittlement can occur. The problem of liquid metal embrittlement is essentially one of eating through the metal with alloying materials (such as tin or germanium) which are extremely corrosive to steel under reducing conditions to the point where, again, the metallurgy fails.

The process of the invention is particularly advantageous due to the use of a treated reactor system which is resistant to carburization even in the absence of added sulfur. By use of the treated equipment, dehydrogenated hydrocarbons may be produced for significantly longer periods of time without requiring a shut down of the process due to coking, carburization and metal-dusting which occurs at dehydrogenation conditions using dehydrogenatable hydrocarbons. Thus, increased amounts of dehydrogenated hydrocarbons, such as butylene, may be produced.

Furthermore, higher temperatures may be used during dehydrogenation allowing for increased olefin production. In fact, temperatures required to dehydrogenate propane (i.e., reaction temperatures of 1200° F. and higher) may be used without excessive coking, carburization and metal-dusting. Accordingly, the invention can provide a process for catalytically dehydrogenating a hydrocarbon such as ethane, propane, n-butane, isobutane, mixed butanes, pentanes, isopentanes, detergent range paraffins, and ethylbenzene to a dehydrogenated olefinic product where carburization resistance will be maintained at skin temperatures of the reactor system of above 1200° F., and even above 1300° F. Preferred hydrocarbons are $C_3$ and $C_4$ hydrocarbons.

The present invention is particularly useful for dehydrogenation processes that occur in abrasive environments, such as those found in the Oleflex ™ process.

The Oleflex ™ process has a catalyst bed which continuously moves from reactor to regenerator. Oxidation and oxychlorination occur during regeneration. The protective layers used according to the invention would be able to withstand the abrasion associated with the movement of catalyst through reactors such as moving bed and fluidized bed reactors. Preferably, the coatings resist abrasive damage for a period sufficient to protect against carburization for at least 200 hours, preferably at least 500 hours and more preferably at least 800 hours of operation.

Furthermore, it has been discovered that preferred tin-based coatings of this invention, upon oxidation, produce persistent, hard and abrasion resistant mixed metal oxide coatings. Surprisingly, these coatings remain fixed to the metal surfaces during oxidation/reduction cycles. These hard oxide coatings are also effective in protecting the metal surface from carburization, metal dusting and coking. Therefore, the preferred protective layers are useful in reducing environments, in oxidizing environments, and in environments that cycle between oxidation and reduction, as often encountered in dehydrogenation processes.

Additionally, it has now been surprisingly found that preferred coatings of this invention are sulfur-tolerant, for example, the tin-based protective layers can tolerate up to 200 ppm sulfur in the feed. The protective layers eliminate the need to presulfide the metallurgy, reduce sulfide corrosion, and improve product values and waste disposal due to reduced levels of sulfur. Chromium-, Sb- and Ge-based protective layers can tolerate even higher sulfur levels, up to 5 or more wt %. Most preferably, the layers can tolerate the respective amounts of sulfur for a period of at least 200 hours, more preferably at least 400 hours, and most preferably at least 600 hours without degrading to an extent that carburization will occur resulting in shut-down of the system due to excessive coking. On the other hand, the protective layers are also extremely effective for protecting metal surfaces at low sulfur and ultra-low sulfur levels. Thus, the protective layers allow a variety of sulfur levels to be used in the reactor system and provides significantly increased versatility in catalyst selections (S tolerant vs. S intolerant). It is not necessary to add sulfur to the system. The ability to operate at low sulfur levels also can improve catalyst performance, e.g., increase selectivity and conversion.

With the foregoing, as well as other objects, advantages, features and aspects of the disclosure that will become hereinafter apparent, the nature of the disclosure may be more clearly understood by reference to the detailed description and the appended claims.

BRIEF DESCRIPTION OF THE DRAWING

The figure shows a stainless steel substrate having provided thereon a protective stannide layer which is anchored to the steel substrate through an intermediate carbide-rich, nickel-depleted bonding layer.

DETAILED DESCRIPTION OF THE PREFERRED EMBODIMENTS

The following description is merely illustrative of preferred embodiments of the invention and should not be considered as limiting the scope of the invention in any way, as the illustrations and other equivalents thereof will become more apparent to those versed in the art in light of the disclosure, and the accompanying claims.

As indicated above, the invention is directed to an improved method for dehydrogenation. The method includes providing metallic protective layers to at least a portion of the reactor system which impart long-term carburization, embrittlement and metal-dusting protection, even at the high skin temperatures of furnace tubes used in dehydrogenation systems.

Hydrocarbons which may be dehydrogenated according to the invention include hydrocarbons having 2–30 or more carbon atoms containing at least one pair of adjacent carbon atoms, each having a hydrogen attached thereto. Preferably, the hydrocarbons include ethane, propane, n-butane, isobutane, mixed butanes, pentanes, isopentanes, detergent range paraffins, hexane and ethylbenzene. Preferred are butanes and propanes. These hydrocarbons may also include normal paraffins up to $C_{30}$ normal paraffins, branched paraffins, normal olefins, branched olefins, diolefins, polyolefins, and the like hydrocarbons. Thus, it is intended to include within the scope of the invention the dehydrogenation of any organic compound capable of being dehydrogenated to produce olefinic products containing the same number of carbon atoms but fewer hydrogen atoms. Examples may include isobutane, isopentane, isohexane, 2-methyl-1-dodecane, and the like hydrocarbons and cyclobutane, cyclopentane, cyclododecane, and the like hydrocarbons.

Such dehydrogenated hydrocarbons also include those utilized to make tackifying agents for adhesives, viscosity-index additives for motor oils and impact-resistant and anti-oxidant additives for plastics. Dehydrogenated hydrocarbons may also be used in the manufacture of various chemical products such as detergents, plastics, synthetic rubbers, pharmaceutical products, high octane gasoline, perfumes, drying oils, ion-exchange resins, and various other products well known to those skilled in the art.

The dehydrogenatable hydrocarbons are contacted with a catalytic composite in a dehydrogenation zone maintained at dehydrogenation conditions. This contacting may be accomplished in a fixed catalyst bed system, a moving catalyst bed system, a fluidized bed system, or in a batch-type operation. The dehydrogenation reaction zone itself may comprise one or more separate reactor zones with heating means therebetween to ensure that the temperature can be maintained at the entrance to each reaction zone to obtain the desired conversion. The hydrocarbon may be contacted with the catalyst composite in either upward, downward or radial flow fashion. The hydrocarbon may be in the liquid phase, a mixed vapor-liquid phase or the vapor phase when it contacts the catalyst. Preferably, the hydrocarbon is in the vapor phase.

Dehydrogenation conditions include a temperature of from about 300° F. to about 1500° F., a pressure of from about 0.001 to about 25 atmospheres and a liquid hourly space velocity (LHSV) of about 0.01 to about 50 $hr^{-1}$. Preferred temperatures are from about 750° F. to about 15000° F., more preferably, about 900° F. to about 1450° F., and most preferably 1050° F. to 1250° F. In the case of the lowest molecular weight hydrocarbons, e.g., propane, the higher temperatures are employed. For example, temperatures greater than about 10000° F. and preferably between 1100° F. to 1400° F. may be preferred when dehydrogenating propane or butane. Preferred pressures range from about 0.1 atmospheres to about 5 atmospheres. Atmospheric pressure is very suitable in most processes. Preferred LHSV range from about 0.2 hr$^{-1}$ to about 30 hr$^{-1}$, even more preferably, from about 1 to about 5 hr$^{-1}$.

Of course, those skilled in the art will choose the desired temperature, pressure and LHSV depending on the hydrocarbon feed and catalyst systems utilized. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The dehydrogenatable hydrocarbons may be admixed with a diluent gas before, while or after being passed to the dehydrogenation zone. The diluent material may be hydrogen, steam, methane, carbon dioxide, nitrogen, argon or the like, or a mixture thereof. When a diluent gas is utilized, amounts sufficient to ensure a diluent gas to hydrocarbon mole ratio of about 0.1 to about 20, with best results being obtained when the mole ratio range is about 1 to 10. The diluent hydrogen stream passed to the hydrogenation zone will typically be recycled hydrogen separated from the effluent from the dehydrogenation zone in the hydrogen separation zone.

In conventional dehydrogenation processes, sulfur-containing gases such as $H_2S$ and hydrogen have been added to prevent coking throughout the reactor system. In the methods according to the invention, low sulfur levels are preferred. Sulfur and hydrogen may be added to the feed. However, neither sulfur nor hydrogen are required to inhibit carburization. In fact, it is preferred that less than 100 ppm sulfur, and more preferably, less than 50 ppm sulfur be present in the feed, and even more preferably, less than 20 ppm sulfur. Thus, the process may be conducted under reduced amounts or even in the absence of added sulfur and hydrogen.

When using the large-pore zeolite catalysts, which are further discussed below, feeds containing low amounts of sulfur are preferred. Preferably, the feed will contain less than 10 ppm sulfur, more preferably, less than 5 ppm sulfur, and even more preferably, less than 1 ppm sulfur. If necessary, a sulfur sorber unit may be employed to remove sulfur.

The dehydrogenation catalyst composite should exhibit high activity, high selectivity and good stability. Particularly preferred catalytic composites of the present disclosure include those composites comprising roup VIII noble metals and a solid inorganic carrier. Such catalytic composites are well known to those skilled in the art as represented by U.S. Pat. Nos. 3,531,543; 3,631,215; 3,864,284; 3,584,060; 4,191,846; 4,595,637; 4,716,143; 4,786,625; 4,827,072; and 4,902,849, the contents of which are incorporated herein by reference. Particularly preferred catalyst composites include the platinum on alumina catalysts and chrome on alumina catalyst.

When using feeds containing no or negligible sulfur, there may be used the so-called sulfur sensitive large-pore zeolite type catalyst composites charged with one or more dehydrogenating constituents patented by Chevron Research are useful. See, e.g., U.S. Pat. No. 4,727,216.

The term "large-pore zeolite" is indicative generally of a zeolite having an effective pore diameter of 6 to 15 Angstroms. Preferable large pore crystalline zeolites which are useful in the present invention include the type L zeolite, zeolite X, zeolite Y and faujasite. These have apparent pore sizes on the order of 7 to 9 Angstroms. Most preferably, the zeolite is a type L zeolite.

The type L zeolite, its x-ray diffraction pattern, its properties, and method for its preparation are described in detail in, e.g., U.S. Pat. No. 3,216,789, the contents of which are hereby incorporated by reference. Zeolite Y is described in more detail in U.S. Pat. No. 3,130,007 the contents of which is hereby incorporated by reference. Zeolite X, its X-ray diffraction pattern, its properties, and method for its preparation are described in detail in U.S. Pat. No. 2,882,244 the contents of which are hereby incorporated by reference.

An alkali and/or alkaline earth metal is preferably present in the large-pore zeolite. Preferred alkali metals include potassium, cesium, and rubidium, with potassium being especially preferred. The alkaline earth metal may be either barium, strontium or calcium, preferably barium. The alkali metal and/or alkaline earth metal can be incorporated into the zeolite by synthesis, impregnation or ion exchange. Barium is preferred to the other alkaline earths because it results in a somewhat less acidic catalyst. Strong acidity is undesirable in the catalyst because it promotes cracking, resulting in lower selectivity.

In another embodiment, at least part of the alkali metal can be exchanged with barium using known techniques for ion exchange of zeolites. This involves contacting the zeolite with a solution containing excess Ba$^{++}$ ions. In this embodiment, the barium should preferably constitute from 0.1% to 35% by weight of the zeolite.

The large-pore zeolitic catalysts used in the dehydrogenation process may be charged with one or more Group VIII metals, e.g., nickel, ruthenium, rhodium, palladium, iridium or platinum. The preferred Group VIII metal is platinum. If used, the preferred weight percentage of platinum in the catalyst is between 0.1% and 5%, and more preferably between 0.2 and 1.5%.

Group VIII metals are introduced into large-pore zeolites by synthesis, impregnation or exchange in an aqueous solution of appropriate salt. When it is desired to introduce two Group VIII metals into the zeolite, the operation may be carried out simultaneously or sequentially.

While the above described catalyst composites are preferred, other dehydrogenation catalysts known to those skilled in the art may be used. Such dehydrogenation catalysts include those catalysts suitable for use in dehydrogenation processes such as the Air Products Catafin ™ process and the Phillips Star ™ process.

Optionally, the catalyst composite may also contain other, additional components or mixtures thereof which act along or in concert as catalyst modifiers to improve catalyst activity, selectivity or stability. The catalyst modifiers are preferably, but not necessarily, dispersed throughout the catalyst composite in a uniform distribution. Some well-known catalyst modifiers include antimony, arsenic, bismuth, cadmium, chromium, cobalt, copper, gallium, germanium, gold, indium, iron, manganese, nickel, rhenium, scandium, silver, tantalum, thallium, titanium, tungsten, uranium, zinc and zirconium. These additional components may be added in any suitable manner to the carrier material during or after its preparation or they may be added in any suitable manner to the catalytic composite either before, while or after other catalytic components are incorporated.

Tin may also be used as a modifier of the catalyst composite. In this regard, it is known to add tin to catalysts to inhibit isomerization and the cracking activities normally concurrently experienced in the use of unmodified noble metal composites in the dehydrogenation of hydrocarbon feeds in the vapor phase at elevated temperatures. See, e.g., U.S. Pat. No. 3,531,543 and U.S. Pat. No. 4,717,216. The tin modifier component may be present as an elemental metal, as a chemical compound such as an oxide, sulfide, halide, oxychloride, etc., or as a physical or chemical combination of the porous carrier material and/or other components of the catalytic composite. The tin modifier component is preferably utilized in an amount sufficient to result in a final catalytic composite containing about 0.01 to about 10 weight percent tin, calculated on an elemental basis, with best results obtained at levels of about 0.1 to about 5 weight percent.

Optionally, the catalyst used in the present invention may contain a sulfur component. Generally, the sulfur component may comprise about 0.01 to 2 weight percent, calculated on the elemental basis, of the final catalytic composite. The sulfur component may be incorporated into the catalytic composite in any suitable manner, preferably, sulfur or a compound containing sulfur such as hydrogen sulfide or a lower molecular weight mercaptan, for example, is contacted with the catalyst composite in the presence of hydrogen at a hydrogen to sulfur molar ratio of about 100 and a temperature of from about 10° to about 140° C., preferably under water-free conditions, to incorporate the sulfur component. Preferably, however, the catalyst composite does not include a sulfur component. In this regard, sulfur free catalyst systems are particularly preferred. However, even when using the so-called sulfur sensitive catalyst composites, the composite may be sulfided prior to use.

In the petrochemical industry, a "dehydrogenation process" involves the removal of hydrogen from a reactant to produce an unsaturated bond without the formation of substantial mounts of aromatic moieties (i.e., not more than 10%, preferably not more than 5%, and even more preferably not more than 1%). By "reactor system" as used herein there is intended at least one dehydrogenation reactor and its corresponding piping, furnaces, furnace tubes, heat exchangers, and the like effective to remove hydrogen from a reactant to produce an unsaturated bond without the formation of substantial amounts of aromatic moieties. Frequently, substantial portions of dehydrogenation reactor systems including the reactors themselves are constructed of stainless steels. Stainless steels as defined by The American Society for Metals in the Metals Handbook, Desk Edition (1985), are those steels containing at least 10% chromium with or without other elements. However, in the United States, it is customary to include with stainless steels those alloys that contain as little as 4% chromium. Thus, as used herein stainless steels are those steels which include at least 4% chromium, preferably at least 10% chromium.

Preferred stainless steels contain nickel, generally –10% nickel. These steels include the so-called "300 Series" stainless steels, such as 304, 316, 316H and 347. Steels with substantially higher nickel contents, such as Incoloy steels, are not as useful in this invention. The high nickel content results in excessively nickel-rich stannides in the protective layer which come in contact with hydrocarbons during operation. Very nickel-rich stannides are themselves coke producers and thus can result in plugging of the reactor system.

Nickel-free steels including chromium molybdenum steels, such as 9 chrome/1 moly or 400 series steels such as 410, 420, 430 and 446 steels, can also be protected according to the invention. As with stainless steels, a carburization resistant protective layer is provided to a thickness effective to completely cover the surface of the steel and isolate the steel from hydrocarbons, while avoiding those thicknesses which lead to substantial liquid metal embrittlement. The protective layer on nickel-free steels is anchored to the steel through an intermediate carbide-rich bonding layer that contains carbide inclusions. This intermediate bonding layer is typically chromium-enriched relative to the steel.

Because the protective layers are exposed to the relatively harsh conditions of dehydrogenation processes (e.g., high temperatures), the protective layers must be of sufficient thickness to provide a substantially complete coating of the underlying base metal. Even minor imperfections, pinholes or other flaws in the protective layer can provide destructive carburization sites sufficient to shut-down operation.

In fact, it has been observed that at the interface between a stannideprotected portion of steel and unprotected portion, relatively deep pitting and carburization attack occurs; surprisingly more so than anywhere else across the rest of the unprotected steel surface. This suggests that an incompletely protected system is even more vulnerable to metallurgical failure than a wholly unprotected system.

The application of excessive amounts or thicknesses of the material used to form the protective layer must also be avoided. If the layer is too thick, liquid metal embrittlement can occur.

The protective layer must also maintain its integrity through operation. As such, the protective coating must be sufficiently abrasion resistant during catalyst loading, start-up, as well as during operation (e.g., it should be resistant to the abrasive effects of the catalyst moving through the reactor). This is achieved through appropriate anchoring of the protective layer to the steel substrate. According to the invention, the protective layer can be anchored to the steel substrate through an intermediate carbide-rich bonding layer.

Effective protective layers can be derived from a variety of metals such as tin, copper, arsenic, antimony, bismuth, chromium, brass, germanium, gallium, indium, selenium, tellurium, lead and intermetallic compounds and alloys thereof, more preferably tin, germanium, antimony, arsenic, selenium, chromium and tellurium. Of these, tin, germanium and antimony are more preferred, with tin being the most preferred. Gallium, lead, bismuth, brass, indium and copper are less preferred, with brass being the least preferred. Lead, bismuth and indium do not react with iron. They can be used on nickel-rich materials such as INCONEL 600 (75% Ni/16% chromium/7% Fe).

One of these is first applied to a portion (or portions) of a dehydrogenation reactor system as a plating, cladding or coating to a thickness effective to provide a complete coating, while avoiding thicknesses at which liquid metal embrittlement will occur. Then the plating, cladding or coating is treated in a manner effective to form a protective layer which is anchored to the steel substrate thereby providing the necessary abrasion resistance. Preferably, the plating, cladding, or coating is resistant to abrasion, peeling or flaking for a period of 1 year, preferably 2 years, and more preferably 3 years such that the reactor system will maintain its carburization resistant properties without reapplication.

Multiple coatings can be applied. For example, a tin coating can be applied, and cured, followed by copper plating. Although, it has been found that copper is effective for preventing carburization and metal dusting, it does not generally adhere well to steel. Peeling and flaking of the copper is observed. However, if the steel surface is first coated with tin, then the copper plate will adhere well to the coating, and provide additional protection to the metal surface. In essence, the resulting stannide layer functions as a glue which adheres the copper plate to the underlying steel.

Forming a protective layer according to the invention will depend on temperature treatment after application of the aforementioned metals, and the nature of the base metal.

Taking the application of tin as an example, $Ni_3Sn$, $Ni_3Sn_2$, and $Ni_3Sn_4$ can all be expected in nickel-rich systems, and $Fe_3Sn$, $Fe_3Sn_2$, and $FeSn$ in iron-rich systems. Under temperature exposures of from about 925 to 1200° F., one can expect an $X_3Sn_2$ solid solution on stainless steels. On nickel-free steels there is observed $Fe_3Sn_2$ overlain by $FeSn$. Below 925° F. one can expect $FeSn_2$ but not $Fe_3Sn_2$. On stainless steels there is observed $FeSn$ overlain by $FeSn_2$ overlain by $Ni_3Sn_4$. At high temperatures, e.g., 1600° F., there can be found $(Ni,Fe)_3Sn$ and $(Ni,Fe)_3Sn_2$ on stainless steels, but no steel-tin alloy, while on nickel-free steels there is found a diffusion layer of iron-tin alloy overlain by the phases $Fe_3Sn$ and $Fe_3Sn_2$.

A preferred embodiment of the invention is a method for dehydrogenating hydrocarbons in a reactor system including a stainless steel portion, which comprise providing the stainless steel portion with a stannide protective layer of sufficient thickness to isolate the stainless steel portion from hydrocarbons, which protective layer is anchored to the steel substrate through an intermediate carbide-rich, nickel-depleted stainless steel bonding layer. More particularly, the stannide layer is nickel-enriched and comprises carbide inclusions, while the intermediate carbide-rich, nickel-depleted bonding layer comprises stannide inclusions. More preferably the carbide inclusions are continuous as they extend, substantially without interruption, from the intermediate carbide-rich, nickel-depleted bonding layer into the stannide layer, and the stannide inclusions are likewise continuous extending from the stannide layer into the intermediate carbide-rich, nickel-depleted bonding layer. The interface between the intermediate carbide-rich, nickeldepleted bonding layer and the nickel-enriched stannide layer is irregular, but is otherwise substantially without interruption. The extent to which the aforementioned layers and inclusions develop are a function of the reducing conditions and temperature at which the initial plating, cladding or other coating is treated, and the amount of time at which exposure is maintained.

The plating, cladding or coating of a chromium-rich, nickel-containing steel with a layer of tin in effect creates a double protective layer. An inner chromium rich layer which is resistant to carburization, coking, and metal-dusting and an outer stannide protective layer which is also resistant to carburization, coking and metal-dusting results. This occurs because when exposed to typical dehydrogenation temperatures, such as up to about 1500° F., the tin reacts with the steel to form iron-nickel stannides. Nickel is preferentially leached from the surface of the steel leaving behind a layer of chromium rich steel. In some instances, it may be desirable to remove the iron nickel stannide layer from the stainless steel to expose the chromium rich steel layer.

For example, it was found that when a tin cladding was applied to a 304 grade stainless steel and heated at about 1200° F. there resulted a chromium rich steel layer containing about 17% chromium and substantially no nickel, comparable to 430 grade stainless steel.

The plating, cladding or coating may be applied by methods including electroplating, vapor depositing, and soaking of the chromium rich steel in a molten metal bath. When applying the tin metal to the chromium rich steel, it may be desirable to vary the thickness of the metal plating, cladding or coating to achieve the desired resistance against carburization, coking, and metal-dusting. This can be done by, e.g., adjusting the amount of time the chromium rich steel is soaked in a molten tin bath. This will also affect the thickness of the resulting chromium rich steel layer. It may also be desirable to vary the cure temperature, or to vary the composition of the chromium rich steel which is coated in order to control the chromium concentration in the chromium rich steel layer produced.

It has additionally been found that stannide protected steels can be further protected from carburization, metal-dusting, and coking by a post-treatment process which involves application of a thin oxide coating, preferably a chromium oxide, such as $Cr_2O_3$. This coating will be thin, as thin as a few $\mu$m. The chromium oxide layer can be applied by various methods including: application of a chromate or dichromate paint followed by a reduction process; vapor treatment with an organo-chromium compound; or application of a chromium metal plating followed by oxidation of the resulting chromium plated steel.

Where practical, it is preferred that the resistant materials be applied in a paint-like formulation (hereinafter "paint") to a new or existing reactor system. Such a paint can be sprayed, brushed, pigged, etc. on reactor system surfaces such as stainless steels. It is most preferred that such a paint be a decomposable, reactive paint which reduces to a reactive metal preferably forming metallic stannides (e.g., iron stannides and nickel/iron stannides) upon heating in a reducing atmosphere.

In addition to applied thickness, viscosity and other properties of the paint are important. The viscosity should be such that the paint can be easily applied and that it does not drip or pool due to gravity. The paint should also be dryable once applied to the reactor surfaces. The thickness of the paint after application should be between 0.5 and 15 mils, preferably between 1 and 10 mils, and most preferably between 2 and 8 mils.

The metallic coatings and, in particular, the paints, are preferably produced under reducing conditions with hydrogen. Curing is preferably done in the absence of hydrocarbons. When tin paints are applied at the above-described thicknesses, initial reduction conditions will result in tin migrating to cover small regions (e.g., welds) which were not painted. This will completely coat the base metal. This curing results, for example, in a strong protective layer preferably between 0.5 and 10 mils thick, and more preferably between 1 and 4 mils thick comprising intermetallic compounds. In the case of tin, stannide layers such as iron and nickel stannides are formed. Microscopic analysis can readily determine the thickness of this layer. For ease of measurement of paint and coating thickness, coupons can be prepared which correspond to the painted reactor surface. These can be treated under identical conditions to the reactor system treatment. The coupons can be used to determine paint and coating thickness.

For tin-containing paints, it is preferable to initially cure the paint at temperatures below typical operating temperatures for dehydrogenation. Curing temperatures between 500° and 1100° F., preferably between 900° and 1000° F. (especially for oxide-containing paints), provide a carburizationresistant coating that minimizes the incorporation of chromium in the stannide coating (which is undesirable).

As an example of a suitable paint cure, the system including painted portions can be pressurized with $N_2$, followed by the addition of $H_2$ to a concentration greater than or equal to 50% $H_2$. The reactor inlet temperature can be raised to 800° F. at a rate of 50°–100° F./hr. Thereafter the temperature can be raised to a level of 950°–975° F. at a rate of 50° F./hr, and held within that range for about 48 hours. Curing can also be achieved in pure $H_2$ at 1000° F. to 1200° F. for 2–24 hours.

As noted previously, for stannide protective layers, curing temperature will affect the characteristics of the protective layer. Hence, care should be taken in curing the stannide protective layer. For example, in the case of a stannide protective layer applied by plating tin on an INCOLOY 800 substrate (a nickel-rich steel), exposure to low curing temperatures, i.e., three weeks at 650° F. was observed to produce discrete iron and nickel stannide phases; with an unacceptably reactive nickel phase on the exterior. However, exposure at higher temperatures, i.e., one week at 650° F. followed by two weeks at 1000° F., was observed to provide acceptable stannide phases where the stannide was reconstituted to comparable nickel and iron abundance in each stannide phase. Exposure to even higher temperatures, i.e., one week at 650° F. followed by one week at 1000° F. and one week at 1200° F., showed a reconstitution of the stannide layer and carbide-rich under layer, to produce potentially reactive nickel-rich stannides, particularly on the surface of the protective layer. In this regard, it is believed that inclusion of iron, for example, in a paint formulation can be an effective counter-measure when curing and operating at high temperatures.

The metal or metal compounds contained in the plating, cladding or other coating are preferably cured under conditions effective to produce molten metals and/or compounds. Thus, germanium and antimony paints are preferably cured between 1000° F. and 1400° F.

It is most preferred that paints used according to the invention contain at least four components (or their functional equivalents); (i) a hydrogen decomposable tin compound, (ii) a solvent system, (iii) a finely divided tin metal and (iv) tin oxide as a reducible sponge/dispersing/binding agent. The paint should contain finely divided solids to minimize settling, and should not contain non-reactive materials which will prevent reaction of reactive tin with surfaces of the reactor system.

As the hydrogen decomposable tin compound, tin octanoate is particularly useful. Commercial formulations of this compound itself are available and will partially dry to an almost chewing-gum-like layer on a steel surface; a layer which will not crack and/or split. This property is preferable for any coating composition used in this context because it is conceivable that the coated material will be stored for months prior to treatment with hydrogen. Also, if parts are coated prior to assembly they must be resistant to chipping during construction. As noted above, tin octanoate is available commercially. It is reasonably priced, and will decompose smoothly to a reactive tin layer which forms iron stannide in hydrogen at temperatures as low as 600° F.

Tin octanoate should not be used alone in a paint, however. It is not sufficiently viscous. Even when the solvent is evaporated therefrom, the remaining liquid will drip and run on the coated surface. In practice, for example, if such were used to coat a horizontal tube, it would pool at the bottom of the tube.

Component (iv), the tin oxide sponge/dispersing-/binding agent, is a porous tin-containing compound which can sponge-up an organo-metallic tin compound, yet still be reduced to active tin in the reducing atmosphere. In addition, tin oxide can be processed through a colloid mill to produce very fine particles which resist rapid settling. The addition of tin oxide will provide a paint which becomes dry to the touch, and resists running.

Unlike typical paint thickeners, component (iv) is selected such that it becomes a reactive part of the coating when reduced. It is not inert like formed silica; a typical paint thickener which would leave an unreactive surface coating after treatment.

Finely divided tin metal, component (iii), is added to insure that metallic tin is available to react with the surface to be coated at as low a temperature as possible, even in a non-reducing atmosphere. The particle size of the tin is preferably one to five microns which allows excellent coverage of the surface to be coated with tin metal. Non-reducing conditions can occur during drying of the paint and welding of pipe joints. The presence of metallic tin ensures that even when part of the coating is not completely reduced, tin metal will be present to react and form the desired stannide layer.

The solvent should be non-toxic, and effective for rendering the paint sprayable and spreadable when desired. It should also evaporate quickly and have compatible solvent properties for the hydrogen decomposable tin compound. Isopropyl alcohol is most preferred, while hexane and pentane can be useful, if necessary. Acetone, however, tends to precipitate organic tin compounds.

In one embodiment, there can be used a tin paint of 20 percent Tin Ten-Cem (contains 20% tin as stannous octanoate in octanoic acid or neodecanoate in neodecanoic acid), stannic oxide, tin metal powder and isopropyl alcohol.

Iron bearing reactive paints are also useful in the processes of the invention. More particularly, adding finely-ground, particulate iron or dissolved iron to the tin paint is advantageous. It is believed that the iron dilutes nickel in the stannide coating (Ni stannides are not as resistant to coking and metal dusting as Fe stannides) and also reduces the amount of chromium drawn from the steel into the coating. By adding particulate iron or dissolved iron, protection is enhanced due to the formation of Fe stannides. When adding iron to tin paints, it is preferred that the weight ratio of tin to iron in the paint be between 10/1 and 1/1, preferably between 5/1 and 2/1. Preferred iron compounds include finely divided iron and iron oxide powders; iron salts, such as $FeCl_3$; and organometallic iron compounds, such as ferrocene.

Adding iron to a tin containing paint affords noteworthy advantages; in particular: (i) it facilitates the reaction of the paint to form iron stannides thereby acting as a flux; (ii) it dilutes the nickel concentration in the stannide layer thereby providing better protection against coking; and (iii) it results in a paint which affords the anti-coking protection of iron stannides even if the underlying surface does not react well.

As mentioned above, other resistant metals such as copper, arsenic, antimony, bismuth, chromium, brass, germanium, gallium, chromium, indium, lead, selenium, tellurium and mixtures thereof, may be employed in or as the protecting coating. For example, antimony and germanium paints can be prepared using antimony and germanium metal sulfides, oxides, halides or mixtures thereof. Reduction at temperatures between 1000° F. to 1400° F. results in excellent adhesion of these metallic coating to the reactor system surfaces. In part, it is believed that sulfide (and halide) paints are especially useful because they are self-fluxing. They, therefore, result in cleanly attached and strongly adherent coatings or intermetallic layers.

Chromium paints are also especially useful in this invention. The use of paints containing chromium halides is preferred, especially chromium chlorides ($CrCl_2$ and $CrCl_3$). Paints based on chromium halides appear to be self-fluxing and form strongly adherent coatings. One advantage of the chromium coatings is that they do not result in liquid metal embrittlement. Chromium paints are preferably reduced at higher temperatures than tin paints in order to produce metallic chromium-containing coatings. Useful reduction temperatures are above 1200° F., preferably at about 1400° F. or higher.

Another technique for obtaining a satisfactory protective layer for use in the present invention is through the use of a novel catalyst load for dehydrogenating a dehydrogenatable hydrocarbon to produce a hydrocarbon product containing the same number of carbon atoms but fewer hydrogen atoms. Again using an anchored stannide protective layer as an example, a catalyst composite can be "surface-treated" with a carburization reducing amount of tin dust. This tin dust will provide a source of tin which will form a protective stannide layer within the reactor system, which can be less than 1 micron thick. The stannide layer prevents or inhibits carburization during the dehydrogenation process. It has been observed that the tin forms a continuous smooth stannide layer on desired surfaces within the reactor system.

Accordingly, by use of the phrase "catalyst load," it is meant a catalyst composite otherwise suitable for dehydrogenating a dehydrogenatable hydrocarbon "surface-treated" with tin dust in an amount effective to reduce or inhibit carburization during the dehydrogenation process. "Surface-treating" includes those means of contact with the catalyst composite which do not involve bonding of the tin dust to or in the composite.

As an example of "surface-treating," catalyst composite particles or the like may be placed into a reactor and tin dust may be dispersed over particles or the like such that the tin dust is in contact with the surface of a catalyst composite and/or in the interstices between adjacent catalyst composite particles.

"Surface-treating" does not include uniformly dispersing elemental tin throughout the catalyst composite or even surface-impregnating tin into a catalyst composite as taught in the prior art. That is, "surface-treating" does not include making the tin dust a physical part of the catalyst composite, i.e., forming a bond between the tin and the remainder of the catalyst composition such that the tin is prevented from forming a stannide layer on surfaces of the reactor system. In this regard, the tin dust used to treat the surface of the catalyst composite should not be confused with a "tin modifier" for the catalyst composite. A tin modifier is a physical part of the catalyst composite used to inhibit isomerization and cracking activities whereas the tin dust is a surface treatment on the catalyst composite used to inhibit coking, carburization and metal-dusting in the reactor system.

Preferably, the tin dust is used in an amount sufficient to inhibit carburization which occurs during dehydrogenation of the dehydrogenatable hydrocarbon. Such amounts may include about 0.1 to about 20 weight percent, but will ultimately depend on the reactor surface to be protected. Of course, the lower the amount used, the better for reasons of economy. The tin dust preferably has a particle size of from about 0.1 to 25 micron. Even more preferably, the tin dust has a particle size of from about 1 to about 5 microns. In any event, the amount and size of the tin dust should be such that a stannide layer is formed on desired surfaces within the reactor system.

Of course, "surface-treating" may be accomplished using other metals that form protective layers on desired surfaces of the reactor system. Such other metals include, but are not limited to antimony, arsenic, bismuth, germanium, indium, lead, selenium and tellurium.

To obtain a more complete understanding of the present disclosure, the following examples illustrating certain aspects of the invention are set forth. It should be understood, however, that the disclosure is not limited in any way to the specific details set forth therein.

EXAMPLE 1

A stannide protective layer was provided on a type 304 stainless steel screen. In particular, the screen sample was tin-plated and exposed to a carburizing atmosphere of 1% toluene in 7% propane in hydrogen. Exposure was continued for 14 weeks at 1150° F., with periodic temperature cycling between high and low temperatures.

Upon completion of the run, the screen sample was mounted in epoxy resin, ground, and polished for examination with petrographic and scanning electron microscopes. No peeling or deleterious chemical alteration of the stannide layer was observed. The Figure is a photomicrographic illustration of the structure of the sample. Three major regions can be identified from the photomicrograph. Reference number 1 identifies the region of the stainless steel substrate. Reference number 2 identifies an intermediate region which is a nickel-depleted, carbide-rich stainless steel bonding layer. Reference number 3 identifies a region which is a nickel-enriched, stannide protective layer. The inclusions identified by reference numbers 4 and 5, appearing in the carbide and stannide phases, respectively, are stannide inclusions (4) and carbide inclusions (5), which anchor the stannide protective layer. As can be seen, substantially all of these inclusions were observed to extend continuously from their source phase. The interface between the intermediate carbide-rich, nickel-depleted stainless steel bonding layer, and the nickel-enriched stannide layer is irregular, but without interruption.

EXAMPLE 2

A stannide type 347 stainless steel coupon of 3 cm length and 1 cm width was painted with a tin-containing paint prepared by mixing together 7 parts by weight Tin Ten Cem (Mooney Chemical Co.), 6 parts by weight isopropyl alcohol, 14 parts by weight tin powder (1–5 microns), 14 parts by weight stannic oxide (−325 mesh) and 5% $Fe_2O_3$. The painted coupon was then reduced in hydrogen for 48 hours at 1000° F. and a cured, carburization and abrasion resistant protective layer was provided. The thickness of the protective layer was observed to be approximately 0.5 to 1 mil. Visual inspection of the coupon confirmed 100% protective layer coverage. The coupon was placed in a reactor where it was subjected to a moving catalyst bed under oxychlorination ($O_2, Cl_2+HCl$ and $H_2$) conditions. The coupon was maintained in this environment for two months at temperatures ranging from 800° F., to temperatures perhaps as high as 2000° F.

The coupon was then removed and examined. It was uniformly gray brown in appearance. It was cut about ¼ inch from the end, and the ¼ inch section was mounted in an epoxy resin, ground, and polished for examination with petrographic and scanning electron microscopies (SEM). Examination of the polished section by reflected light or by electron backscatter image SEM revealed a smooth, continuous coating on all sides of the coupon. This experiment demonstrates that the application of a stannide protective layer according to the invention provides a protective layer which is sufficiently abrasion resistant under commercial-scale conditions.

EXAMPLE 3

Some commercial dehydrogenation processes are operated in halogen containing environments. The presence of halogens adversely affects raw steels. The protective layers of the invention are surprisingly effective for isolating the steels from those halogen effects. Some protective layers of the invention are effective at even high halogen concentrations.

The following tests were run to demonstrate the effectiveness of protective layers for isolating underlying metallurgy from halogen containing environments. The tests were done in a Lindberg quartz tube furnace.

Samples of stainless steel, provided with stannide protective layers and chromium protective layers, were tested at 1000° F. and 1200° F. for twenty-one hours, in the presence of methylchloride. The coupons were placed in an open quartz boat within the hot zone of a tube furnace. The tube was flushed with nitrogen for a few minutes. Then the samples were exposed to a hydrocarbon gas. For experiments using 10,000 ppm halogen, the gas was a 1% $CH_3Cl$ in hydrogen. For those using 1,000 ppm halogen, the gas was a mixture of 0.1% $CH_3Cl$ in 7% propane in hydrogen. Gas flows were 25 to 30 cc/min. at atmospheric pressure. The samples were rapidly brought to operating temperatures.

The test results are shown in the following Table. A "pass" result means the samples did not form substantial amounts of coke on the metal surface.

TABLE

Effect of Chloride

| Ex. No. | Amount of MeCl, ppm | Temp. °F. | Raw Steel | Stannide Protective Layer | Chromium-Protective Layer |
|---|---|---|---|---|---|
| 1 | 10,000 | 1000 | Fail | Pass | Pass |
| 2 | 10,000 | 1200 | Fail | Fail | Pass |
| 3 | 1,000 | 1200 | Fail | Pass | Pass |

The results show that a stannide protected steel can withstand high halogen concentrations at 1000° F., but the protective layer is not as effective at 1200° F. Chrome protective layers were effective under all conditions tested.

Comparative Example 1

A reactor tube made of 0.25 inch OD 316 stainless steel seamless pipe 8.75 inches long was prepared by cleaning the surfaces of the reactor to be exposed to hydrocarbons with soap and water, and drying with an organic solvent. The reactor was preheated and maintained at 1250° F. Toluene at 25 µl/min was fed into the reactor with hydrogen at 20 cc/min. The reactor pressure was maintained at approximately 100 psig. The reactor was completely plugged with coke formed by carburization when checked after 65.6 hours of operation.

Comparative Example 2

A reactor tube was prepared as described in Comparative Example 1. The reactor was pretreated and maintained at 1400° F. Again, toluene at 25 µl/min was fed into the reactor with hydrogen at 20 cc/min. The reactor pressure was maintained at approximately 100 psig. The reactor was completely plugged with coke due to carburization when checked after 5.7 hours of operation.

EXAMPLE 4

A reactor tube made of 0.25 inch OD 316 stainless steel seamless pipe 8.75 inches long was prepared by cleaning the surfaces of the reactor to be exposed to the hydrocarbons with soap and water, and drying with an organic solvent. The reactor was then coated by pouring a tin paint into one end of the reactor, draining the excess, pouring the tin paint into the other end of the reactor, draining the excess, and then curing the coating at approximately 1050° F. for approximately 40 hours. The tin paint used for coating the reactor was prepared by mixing together by weight 7 parts Tin Ten Cem (Mooney Chemical, Co.), 6 parts isopropyl alcohol, 14 parts tin powder (1–5 microns) and 14 parts stannic oxide (−325 mesh) and 5% $Fe_2O_3$ in paint mixture. Toluene at 24 µl/min was fed into the reactor with hydrogen at 20 cc/min for approximately 596 hours of operation at 1400° F. No plugging occurred but operational problems in letdown system caused shutdown.

EXAMPLE 5

A reactor tube was prepared as described in Example 4 except that no $Fe_2O_3$ was used in the paint. Into the reactor which was maintained at 1250° F. and 100 psig, toluene at 25 µl/min and hydrogen at 20 cc/min were introduced for approximately 88 hours of operation. Then, the temperature was raised to 1400° F. The reaction was continued until approximately 303 hours of operation occurred. No plugging of the reactor occurred.

EXAMPLE 6

A reactor tube was prepared as described in Example 4. The reactor was preheated and maintained at a temperature of 1400° F. Toluene at 25 μl/min was fed into the reactor with hydrogen at 10 cc/min. The reactor pressure was maintained at approximately 100 psig. The reaction was allowed to proceed for at least 597 hours before changing the feed to n-hexane. No plugging of the reactor occurred during approximately 600 hours of operation.

EXAMPLE 7

A reactor tube was prepared as described in Example 5. The reactor was preheated and maintained at 1400° F. Toluene containing 50 ppm $CS_2$ at 25 μl/min was fed into the reactor with hydrogen at 10 cc/min. The reaction pressure was maintained at approximately 100 psig. After approximately 44 hours of operation, the amount of $CS_2$ in the toluene feed was reduced to 5 ppm. After approximately 719 hours of operation, the amount of $CS_2$ in the toluene feed, was reduced to 0.5 ppm. The reactor was not plugged upon reading approximately 1079 hours of operation, but plugged upon reading approximately 1219 hours of operation due to an operational problem in the letdown system.

EXAMPLE 8

A reactor tube was prepared as described in Example 5. The reactor was preheated and maintained at approximately 1400° F. Toluene containing 50 ppm $CS_2$ at 25 μl/min was fed into the reactor with hydrogen of 10 cc/min. The reactor pressure was maintained at approximately 100 psig. The reactor was shut down upon reaching approximately 695 hours of operation. No plugging occurred.

The sulfur had no detectable effect on the protective layer when viewed by microscopy.

Comparative Example 3

A platinum loaded L-zeolite catalyst composite was modified by the addition of 0.25 wt % of a tin modifier. The catalyst composite was used as crushed particles having a 24–42 mesh with a bulk density of about 0.7 grams/cc. The catalyst composite was also presulfided. At a reactor temperature of 1100° F., atmospheric pressure, 5 LHSV and $H_2$/HC ratio of 3/1, isobutane was fed into a quartz reactor using the tin-modified sulfided catalyst composite. The tin-modified sulfided catalyst composite converted 50% of the isobutane with 88% selectivity of the product to isobutylene.

Comparative Example 4

Comparative Example 3 was repeated at a reactor temperature of 1050° F. The tin-modified sulfided catalyst composite converted 35% of the isobutane with 92% selectivity of the product to isobutylene.

Comparative Example 5

Comparative Example 3 was repeated at a reactor temperature of 1100° F. in a stainless steel reactor. The tin-modified sulfided catalyst converted 42% of the isobutane with 79% selectivity of the product to isobutylene.

Comparative Example 6

Comparative Example 3 was repeated with an unsulfided catalyst composite and an isobutane feed with 50 ppm $H_2S$ in a stainless steel reactor at 1100° F. The catalyst composite converted 18% of the isobutane with a 94% selectivity of the product to isobutylene. This example shows the detrimental effect of sulfur in the hydrocarbon feed.

EXAMPLES 9–11

In Example 9, Comparative Example 6 was repeated with a catalyst surface-treated with 10 wt % "Pixie Dust", a 1–5 micron size tin powder and without sulfur in the feed. The surface-treated catalyst composite converted 50% of the isobutane with 93% selectivity of the product to isobutylene without coke plugging for over two hundred hours. In Example 10, Example 9 was repeated. The surface-treated catalyst composite converted 46% of the isobutane with 94% selectivity of the product to isobutylene without coke plugging for over two hundred hours. In Example 11, Example 9 was repeated at a reactor temperature of 1150° F. The surface-treated catalyst composite convened 57% of the isobutane with 94% selectivity of the product to isobutylene without coke plugging for over two hundred hours.

EXAMPLE 12

An L-zeolite catalyst composite modified by the addition of 0.25 wt % of a tin modifier. The catalyst composite was used as crushed particles having a 24–42 mesh with a bulk density of about 0.7 grams/cc. At a reactor temperature of 1200° F., atmospheric pressure, 5 LHSV and $H_2$/HC ratio of 1/1, propane was fed into a tin coated stainless steel reactor using the surface-treated catalyst composite. The surface-treated catalyst composite converted 48% of the propane with 88% selectivity to propylene with no sulfur in the system and no coke plugging for the length of the run, i.e., about 120 hours.

While the invention has been described above in terms of preferred embodiments, it is to be understood that variations and modifications may be used as will be appreciated by those skilled in the art. Essentially, therefore, there are many variations and modifications to the above preferred embodiments which will be readily evident to those skilled in the art and which are to be considered within the scope of the invention as defined by the following claims.

What is claim is:

1. A method for dehydrogenation comprising:
   (i) providing a carburization and abrasion resistant protective layer to a steel portion of a dehydrogenation reactor system by (a) applying to the steel portion a metal plating, cladding or other coating of a metal effective for forming a carburization resistant protective layer, to a thickness effective to isolate the steel portion from hydrocarbons during operation while avoiding any substantial liquid metal embrittlement, and (b) forming the protective layer, anchored to the steel portion through an intermediate carbide-rich bonding layer;
   (ii) catalytically dehydrogenating a dehydrogenatable hydrocarbon.

2. A method according to claim 1, comprising dehydrogenating in a fluidized or moving catalyst bed reactor.

3. A method according to claim 1, comprising dehydrogenating hydrocarbons selected from ethane, propane, n-butane, isobutane, mixed butanes, pentanes, isopentanes or ethylbenzene to an olefinic product.

4. A method according to claim 3, comprising dehydrogenating n-butane, isobutane or mixed butanes.

5. A method according to claim 3, comprising dehydrogenating propane.

6. A method according to claim 1, wherein sulfur levels in the reactor system during dehydrogenation do not exceed about 100 ppm.

7. A method according to claim 6, wherein sulfur levels do not exceed about 50 ppm.

8. A method according to claim 7, wherein sulfur levels do not exceed about 20 ppm.

9. A method according to claim 1, wherein the metal is applied as a plating, cladding or other coating comprising at least one metal in major proportion selected from the group consisting of antimony, arsenic, bismuth, copper, chromium, gallium, germanium, indium, lead, selenium, tellurium, tin and mixtures thereof.

10. A method according to claim 9, wherein the metal is applied as a plating, cladding or other coating comprising at least one metal in major proportion selected from the group consisting of antimony, arsenic, chromium, germanium, selenium, tellurium, tin and mixtures thereof.

11. A method according to claim 10, wherein the metal is applied as a plating, cladding or other coating comprising at least one metal in major proportion selected from the group consisting of antimony, germanium, tin and mixtures thereof.

12. A method according to claim 9, wherein the metal plating, cladding or other coating is applied to a thickness of between 0.5 mils and 15 mils.

13. A method according to claim 12, wherein the metal plating, cladding or other coating is applied to a thickness of between 1 and 10 mils.

14. A method according to claim 13, wherein the metal plating, cladding or other coating is applied to a thickness of between 2 and 8 mils.

15. A method according to claim 1, wherein the protective layer is applied to a portion of the reactor system which exhibits a skin temperature of at least about 1000° F. during dehydrogenation.

16. A method according to claim 15, wherein the protective layer is applied to a furnace tube.

17. A method according to claim 9, wherein the metal is applied as a coating using a catalyst composite surface-treated with a carburization inhibiting amount of a metal dust.

18. A method according to claim 17, wherein said metal dust is tin dust.

19. A method according to claim 18, wherein the catalyst composite is surface-treated with tin dust by dispersing about 1 to about 20 wt % tin dust, based on the weight of the composite, over the surface of said composite, the tin dust comprising 0.1 to 20 micron particles of tin.

20. A method according to claim 19, wherein the catalyst composite is surface-treated with tin dust by dispersing about 5 to about 15 wt % tin dust, based on the weight of the composite, over the surface of said composite, the tin dust comprising 1 to 5 micron particles of tin.

21. A method according to claim 9, wherein the metal is applied as a plating.

22. A method according to claim 9, wherein the metal is applied as a paint.

23. A method according to claim 13, wherein the metal is applied as a tin-containing paint.

24. A method according to claim 13, wherein the metal is applied as a tin-containing paint comprising a hydrogen decomposable tin compound, a solvent system, a finely divided tin metal and tin oxide effective as a sponge/dispersing/binding agent.

25. A method according to claim 23, wherein the paint contains iron.

26. A method according to claim 25, wherein the paint contains tin to iron in a ratio of between 10 and 1.

27. A method according to claim 1, wherein the steel portion is a stainless steel portion and the bonding layer is a carbide-rich, nickel-depleted bonding layer.

28. A method according to claim 1, further comprising forming at least one additional protective layer on the surface of the protective layer.

29. A method according to claim 28, further comprising forming a copper-based protective layer on a stannide protective layer.

30. A method for dehydrogenating a dehydrogenatable hydrocarbon, comprising contacting said hydrocarbon in a reactor system with a dehydrogenation catalyst under low sulfur dehydrogenation conditions, wherein at least a portion of the reactor system in contact with the hydrocarbon has been pretreated with a carburization resistant coating to an extent effective to increase the carburization resistance of the reactor system.

31. A method for dehydrogenating a dehydrogenatable hydrocarbon according to claim 30, comprising dehydrogenating in a reactor system pretreated with a carburization resistant tin coating.

32. A method for dehydrogenating a dehydrogenatable hydrocarbon according to claim 30, comprising dehydrogenating in a reactor system pretreated with a carburization resistant chrome coating.

33. The method for dehydrogenating a dehydrogenatable hydrocarbon according to claim 30, wherein said material is provided as a plating, cladding, paint or other coating, to a base construction material.

34. A method according to claim 30, wherein a tin coating is provided to the base construction material using a catalyst load surface treated with tin.

35. A method for dehydrogenating a dehydrogenatable hydrocarbon according to claim 30, wherein at least a portion of said reactor system is pretreated with a resistant coating comprising antimony, arsenic, bismuth or lead.

36. A method for dehydrogenating a dehydrogenatable hydrocarbon according to claim 30, wherein at least a portion of said reactor system is pretreated with a resistant coating comprising germanium.

37. A method for dehydrogenating a dehydrogenatable hydrocarbon according to claim 30, comprising pretreating at least one furnace tube of the reactor system.

38. A method for dehydrogenation comprising:
(i) providing a carburization and abrasion resistant stannide protective layer to a stainless steel portion of a dehydrogenation reactor system by (a) applying to the stainless steel portion a metal plating, cladding or other coating of tin, to a thickness effective to isolate said stainless steel portion from hydrocarbons during operation while avoiding any substantial liquid metal embrittlement, and (b) forming a nickel-enriched stannide protective layer comprising carbide inclusions, anchored to the stainless steel portion through an intermediate carbide-rich, nickel-depleted stainless steel bonding layer comprising stannide inclusions;

(ii) catalytically dehydrogenating a dehydrogenatable hydrocarbon.

39. A method for dehydrogenation according to claim 38, wherein the carbide inclusions are continuous, extending, substantially without interruption, from the intermediate carbide-rich, nickel-depleted bonding layer into the stannide phase, and the stannide inclusions are continuous, extending, substantially without interruption, from the stannide layer into the intermediate carbide-rich, nickel-depleted bonding layer.

40. A method for dehydrogenation according to claim 39, wherein the interface between the intermediate carbide-rich, nickel-depleted bonding layer and the nickel-enriched stannide layer is irregular, but substantially without interruption.

41. A method according to claim 38, comprising dehydrogenating in a fluidized or moving catalyst bed reactor.

42. A method according to claim 38, comprising dehydrogenating hydrocarbons selected from ethane, propane, n-butane, isobutane, mixed butanes, pentanes, isopentanes or ethylbenzene to an olefinic product.

43. A method according to claim 42, comprising dehydrogenating butane.

44. A method according to claim 42, comprising dehydrogenating propane.

45. A method according to claim 38, wherein sulfur levels in the reactor system during dehydrogenation do not exceed about 100 ppm.

46. A method according to claim 45, wherein sulfur levels do not exceed about 50 ppm.

47. A method according to claim 46, wherein sulfur levels do not exceed about 20 ppm.

48. A method according to claim 38, wherein the tin is applied to a thickness of between 0.5 mils and 15 mils.

49. A method according to claim 48, wherein the tin is applied to a thickness of between 1 and 10 mils.

50. A method according to claim 49, wherein the tin is applied to a thickness of between 2 and 8 mils.

51. A method according to claim 38, wherein the protective layer is applied to a portion of the reactor system which exhibits a skin temperature of at least about 1200° F. during dehydrogenation.

52. A method according to claim 51, wherein the protective layer is applied to a furnace tube or heat exchanger.

* * * * *